United States Patent [19]

Brown et al.

[11] Patent Number: 4,841,987

[45] Date of Patent: Jun. 27, 1989

[54] AUTOMATICALLY RESETTING, FORCE-SENSING PROBE AND RELATED METHOD OF OPERATION

[75] Inventors: Stephen J. Brown, Harrisonburg, Va.; Stanley L. Pond, Berthoud, Colo.

[73] Assignee: Accudent, Inc., Harrisonburg, Va.

[21] Appl. No.: 69,190

[22] Filed: Jul. 2, 1987

[51] Int. Cl.⁴ .............................................. A61B 5/10
[52] U.S. Cl. ...................................... 128/777; 33/514
[58] Field of Search ................................. 128/774–782; 433/32, 68, 72, 214, 215; 33/169 B, 172 E, 513, 514, DIG. 13

[56] References Cited

U.S. PATENT DOCUMENTS

| | | | |
|---|---|---|---|
| 3,058,225 | 10/1962 | Ward | 33/172 |
| 3,943,914 | 3/1976 | Grenfell et al. | 128/2 S |
| 4,058,115 | 11/1977 | Forster | 128/2 S |
| 4,132,224 | 1/1979 | Randolph | 128/774 |
| 4,182,312 | 1/1980 | Mushabac | 433/68 |
| 4,192,321 | 3/1980 | Kerber et al. | 128/776 |
| 4,204,544 | 5/1980 | Feldstein et al. | 128/774 |
| 4,250,895 | 2/1981 | Lees | 128/776 |
| 4,340,069 | 7/1969 | Yeaple | 128/776 |
| 4,459,109 | 7/1984 | Radke | 128/777 |
| 4,622,751 | 11/1986 | Berg | 33/DIG. 13 |
| 4,677,756 | 7/1987 | Simon et al. | 33/169 B |
| 4,708,647 | 11/1987 | Pippin et al. | 433/32 |

FOREIGN PATENT DOCUMENTS

| | | | |
|---|---|---|---|
| 0061218 | 9/1982 | European Pat. Off. | 128/774 |
| 0194083 | 9/1986 | European Pat. Off. | 128/774 |
| 2490949 | 4/1982 | France | 128/781 |

OTHER PUBLICATIONS

"A Pressure-Sensitive Periodontal Probe", Gabathuler et al., Helv. Odant. Acta, Oct. 1971.
"Introduction of a New Periodontal Probe: the Pressure Probe", Van Ier Velden et al., J. of Clin. Peri., 1978.

Primary Examiner—Max Hindenburg
Attorney, Agent, or Firm—Finnegan, Henderson, Farabow, Garrett & Dunner

[57] ABSTRACT

An automatically-resetting force-sensing probe for obtaining a standarized depth measurement of a periodontal pocket which automatically resets after the measurement, and which indicates the level of force exerted by the periodontal tissue at the floor of the pocket upon the probe while the depth measurement of the pocket is taken. A related method of operation is also described.

14 Claims, 3 Drawing Sheets

AUTOMATICALLY RESETTING, FORCE-SENSING PROBE AND RELATED METHOD OF OPERATION

BACKGROUND OF THE INVENTION

I. Field of Invention

This invention relates generally to a force-sensing probe and related method of operation for probing periodontal tissue, and more specifically to a force-sensing probe with automatically resetting force-sensing and force-indicating means for placing in contact with the tissue at a particular level of force, and for sensing and indicating that level of force.

II. Background Information

A prior art force-sensing probe is illustrated in FIG. 1(A). An object of the probe is to enable a clinician to obtain a standarized depth measurement of a periodontal pocket which surrounds a tooth, and which has a floor of periodontal tissue. The probe senses the level of the force at which the probe is placed in contact with the periodontal tissue at the floor of the pocket, and indicates when that level has reached a predetermined level, enabling a clinician to obtain a standardized depth measurement of the pocket by measuring the depth when that level has reached the predetermined level.

As illustrated in the figure, the prior art probe is comprised of a magnetizable member 1, a movable lever 2 which has a probe tip 3 at one end and which pivots around pivot pin 4, a coil 5 wrapped around magnetizable member 1, a power supply 6, a potentiometer 11, an annunciator 7, and a contact point 10. Power supply 6 is coupled to coil 5 causing a current to flow through the coil and magnetizing magnetizable member 1 to generate a magnetic force and releasably hold movable lever 2 in an "engaged" position. As illustrated, the power supply is also coupled in series to the movable lever, to the annunciator, and to the contact point. Movable lever 2 has a beveled surface 8 at one end, and magnetizable member 1 similarly has a beveled surface 9 at one end which is parallel to and flush with the beveled surface of the movable lever when the lever is in the "engaged" position.

To measure the depth of a periodontal pocket with the prior art probe, a clinician places the probe tip of the probe in contact with the periodontal tissue at the floor of the pocket. The periodontal tissue exerts a particular level of force on the probe tip, and the clinician adjusts the placing of the probe until the level of force exerted is equal to a predetermined level, defined as the level of force required to overcome the magnetic force releasably holding the movable lever in the "engaged" position. When the level of force is equal to the predetermined level and the magnetic force is overcome, the lever is caused to pivot around the pivot point and move to a "disengaged" position. In the "disengaged" position, the lever is placed in contact with contact point 10 thereby activating annunciator 7 which preferably consists of a buzzer, a lamp or the like. When activated, the annunciator visibly or audibly indicates that the level of force is equal to the predetermined level, and that the lever has moved to the "disengaged" position. After the lever has moved to the "disengaged" position, the clinician then reads the depth measurement from a depth measuring scale (not shown) incorporated within the probe and placed near the probe tip.

To enable the clinician to adjust the predetermined level of force required to overcome the magnetic force releasably holding the lever in the "engaged" position, a potentiometer 11 is provided. When the potentiometer is adjusted, the current flowing through coil 5 is altered, and the level of the magnetic force releasably holding lever 2 in the "engaged" position is proportionately changed.

A variant prior art probe is illustrated in FIG. 1(B). As illustrated in the figure, the variant prior art probe comprises a slidable permanent magnet 101 to which is attached a cylinder 102 of nonmagnetic material with an extended bore 103 for receiving the threaded end of a stub shaft 104. The opposite end of the stub shaft is attached to knob 105. When the knob is turned in a clockwise direction, the threaded end of the stub shaft is caused to progress within the extended bore thereby sliding the cylinder and the permanent magnet to which the cylinder is attached towards the knob across mountings 106.

The variant prior art probe further comprises a magnetizable member 107 which is fixed to a probe housing 108 by means of mountings 109, a movable lever 110 which pivots around pivot pin 111, a probe tip 112 attached to one end of the movable lever, and a battery 113 which is coupled in series to the movable lever. The battery is further coupled in series to an annunciator 115, and to a contact point 114.

Similarly to the prior art probe illustrated in FIG. 1(A), the movable lever is releasably held in an "engaged" position by a magnetic force exerted by the magnetizable member, and a predetermined level of force is required at the probe tip to overcome the magnetic force. The level of the magnetic force releasably holding the lever in the "engaged" position and hence the predetermined level of force required at the probe tip to overcome the magnetic force proportionately increases as the knob is moved in a counter-clockwise direction causing the slidable magnet to move closer to the magnetizable member. When the level of force at the probe tip is equal to the predetermined level, the lever is caused to pivot to a "disengaged" position, and contact the contact point thereby activating the annunciator. When activated, the annunciator visibly or audibly indicates that the level of force at the probe tip is equal to the predetermined level, and that the lever has moved to the "disengaged" position.

The prior art and variant prior art probes suffer from the disadvantage that the movable levers of such probes must be manually reset from the "disengaged" position to the "engaged" position after each measurement of pocket depth. Since a clinician must make an average of six measurements per tooth, such manual resetting is inefficient.

Another disadvantage is that such probes do not provide a clinician with a precise indication of the level of force at the probe tips of such probes when a depth measurement is taken, making the standardization of that measurement difficult. Instead, such probes only provide the clinician with an indication that the level of force is equal to or greater than the predetermined level, but do not indicate the extent to which the predetermined level is exceeded.

Accordingly, it is an object of the present invention to provide a force-sensing probe for obtaining standardized pocket depth measurements while the force exerted on the probe by the periodontal tissue at the floor of the pockets is equal to a predetermined level which, for each pocket depth measurement, senses and indicates the level of force exerted on the probe by the periodontal tissue at the floor of the pocket while the measurement is taken, and which then automatically resets in preparation for another measurement.

SUMMARY OF THE INVENTION

To achieve the foregoing objects, and in accordance with the purpose of the invention as embodied and broadly described herein, there is provided an automatically-resetting force-sensing probe for probing periodontal tissue comprising: a probe tip for placing in contact with the periodontal tissue at a particular level of force; automatically-resetting force-sensing means coupled to the probe tip for sensing that level of force and for producing a potential difference signal having a magnitude proportional to that level; and force-indicating means coupled to the force-sensing means for receiving that potential difference signal and visibly or audibly indicating the magnitude of the potential difference signal.

A related method of probing a periodontal pocket having a floor of periodontal tissue, and, more specifically, of obtaining a standardized depth measurement of the pocket, is also provided comprising the steps of: (a) placing a probe having force-sensing and force-indicating means in contact with the periodontal tissue at the floor of the pocket at a particular level of force; (b) sensing and indicating that level of force; (c) comparing that level of force with a predetermined level, and adjusting the placing of the probe until that level of force is equal to the predetermined level; (d) measuring the depth of the pocket while that level of force is equal to the predetermined level; and (e) automatically resetting the force-sensing and force-indicating means of the probe in preparation for another depth measurement.

DESCRIPTION OF THE PREFERRED EMBODIMENT

Figure 1A:
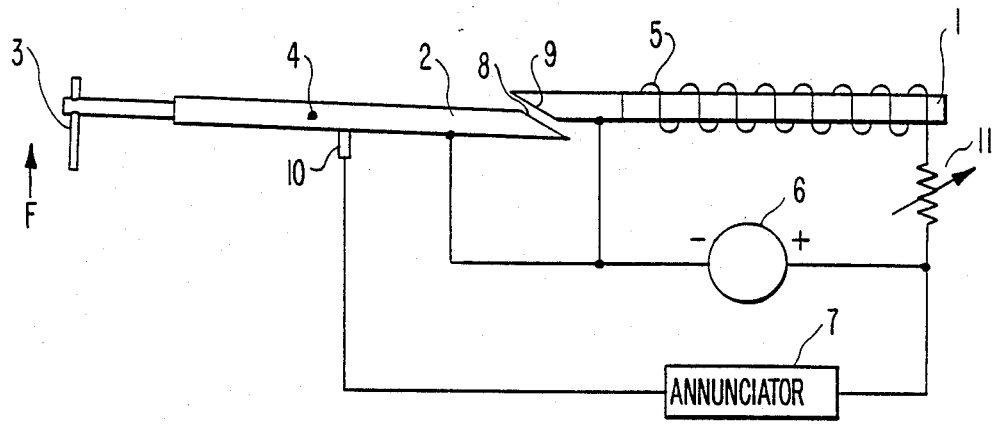
FIG. 1(A) is a schematic drawing of a prior art forcesensing probe.
Figure 1B:
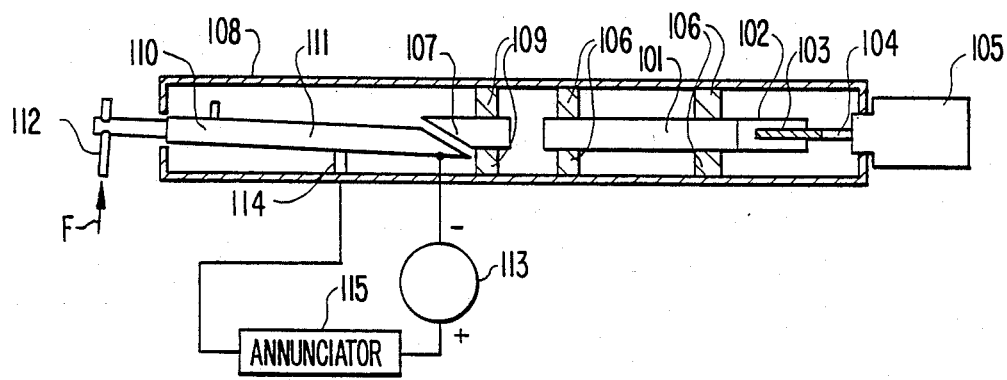
FIG. 1(B) is a schematic drawing of a variant prior art force-sensing probe.
Figure 2A:
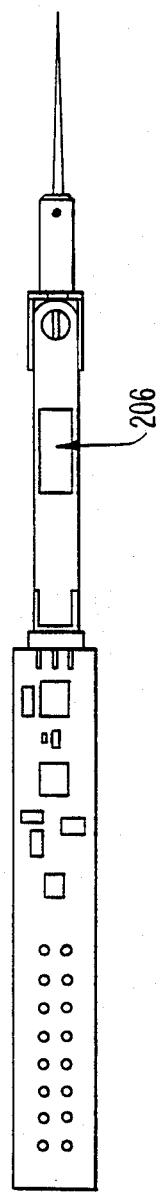
FIG. 2 is a schematic drawing of a force-sensing probe incorporating the teachings of the subject invention.
Figure 2B:
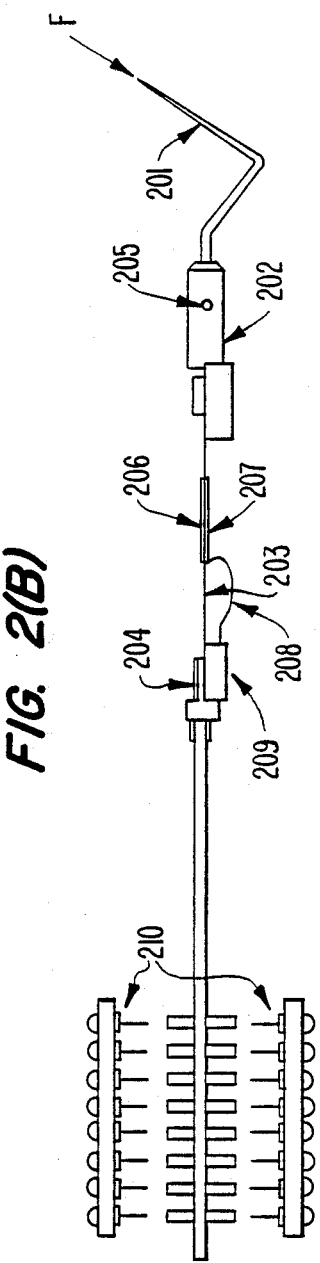

A diagram of a probe incorporating the teachings of the subject invention is illustrated in FIG. 2. As illustrated in the figure, the probe preferably compriss probe tip 201, tip mount 202, bending beam 203, electronics assembly 204, pivot pin 205, strain gauges 206 and 207, flexible conductor 208, connector 209, and a series of light emitting diodes ("LEDs") 210. As shown, the probe tip is preferably coupled to the bending beam through the tip mount and the pivot pin. The strain gauges are mounted on the bending beam, and are coupled to the electronics assembly by means of the flexible conductor and by means of the connector. The electronics assembly is coupled to the series of LEDs.

When probe tip 201 is placed in contact with periodontal tissue, a force F is exerted on the probe tip by the tissue which produces a torque around pivot point 205. The torque, acting through tip mount 202, causes bending beam 203 to bend.

Strain gauges 206 and 207 are preferably coupled to electronic assembly 204 which together produce a potential difference signal having a magnitude proportional to the degree of bending of the bending beam. The strain gauges are coupled to the electronics assembly through flexible conductor 208 and connector 209. In the electronics assembly, the magnitude of the potential difference signal is amplified to produce an amplified potential difference signal having an amplified magnitude, and the amplified potential difference signal is used to light a selected LED within the series of LEDs 210. Each LED within the series has an index, and the index of the selected LED is proportional to the amplified magnitude.

Figure 3:
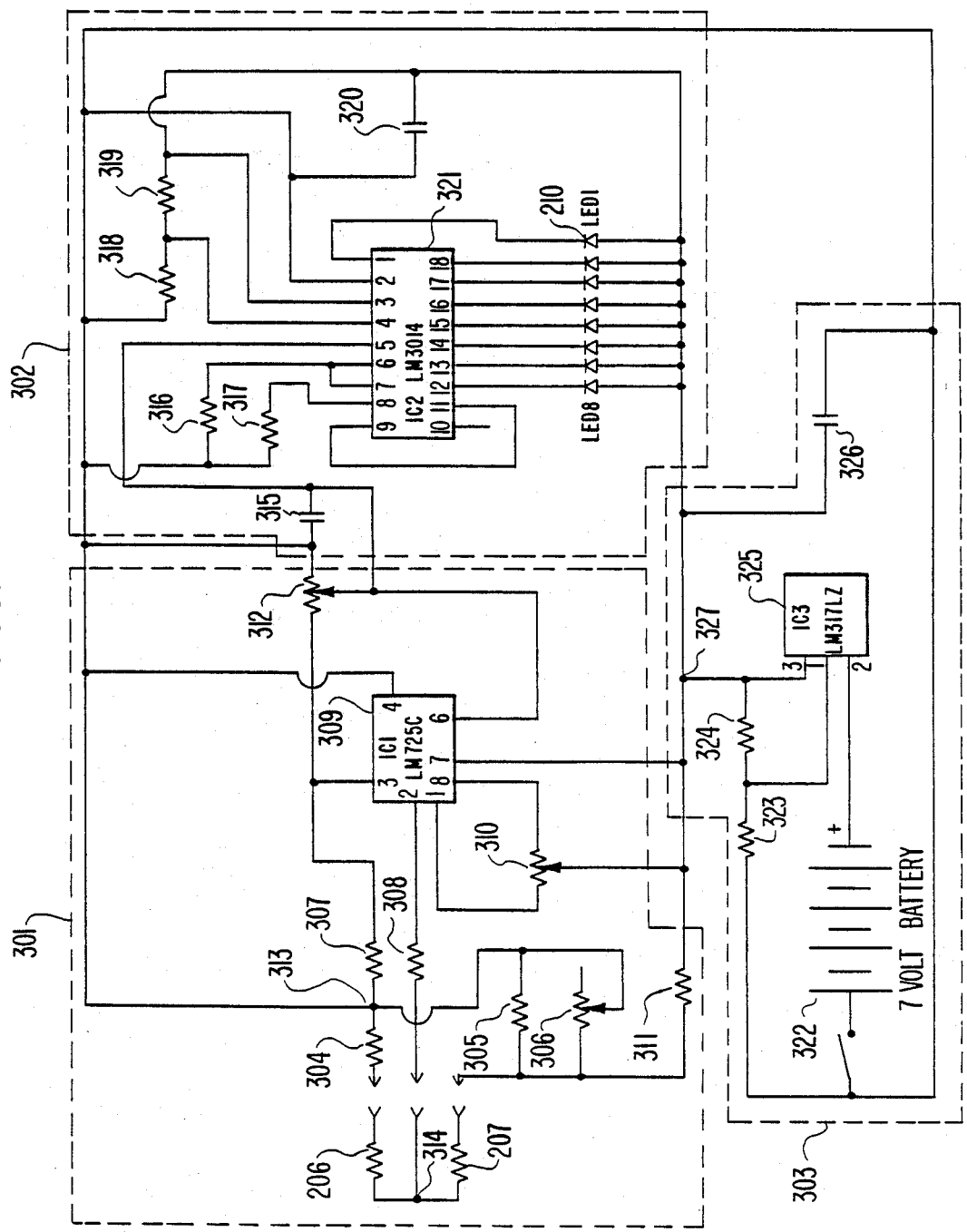
FIG. 3 is a circuit diagram of the electronics assembly of the probe of the subject invention.

A diagram of the electronics assembly is illustrated in FIG. 3. As illustrated in the figure, the electronics assembly preferably comprises amplifying circuitry 301, LED driver circuitry 302, and voltage supply circuitry 303. Also illustrated in the figure are strain gauges 206 and 207 and the series of LEDs 210 (from FIG. 2), which are all coupled to the electronics assembly.

The amplifying circuitry preferably comprises resistor 304, resistor 305, potentiometer 306, resistor 307, resistor 308, operational amplifier 309 having first and second input leads (pins 3 and 2 respectively in FIG. 3) and an output lead (pin 6 in FIG. 3), potentiometer 310, resistor 311, and potentiometer 312.

Strain gauges 206 and 207 are preferably strain gauge resistors whose resistance changes in proportion to the bending of bending beam 203. The strain gauges are coupled to resistor 304, resistor 305, and potentiometer 306 to form a wheatstone bridge having circuit nodes 313 and 314. Circuit nodes 313 and 314 are respectively coupled to the first and second input leads of operational amplifier 309 by means of resistors 307 and 308 respectively.

The wheatstone bridge is balanced by means of potentiometer 306 which is preferably coupled in parallel to resistor 305. The wheatstone bridge is preferably balanced by adjusting potentiometer 306 when no bending of bending beam 203 is present until no potential difference is present between circuit nodes 313 and 314.

When a force is applied to the probe tip and the bending beam is caused to bend, the wheatstone bridge is placed out-of-balance, and a potential difference signal is induced between circuit nodes 313 and 314 having a magnitude which is proportional to the bending of the bending beam and the applied force. The magnitude of the induced potential difference signal is amplified by the operational amplifier to produce an amplified potential difference signal having an amplified magnitude at the output lead of the operational amplifier.

The amplified magnitude of the amplified potential difference signal will preferably range between 1.5 volts (when no force is exerted on the probe tip) to 2.7 volts (when a force having a predetermined level is exerted on the probe tip). The predetermined level is the level chosen with which to standardize periodontal pocket depth measurements, and preferably ranges from 3 to 130 grams. The amplified magnitude will preferably be adjusted to 1.5 volts by means of potentiometer 310 when no force is exerted on the probe tip, and will preferably be adjusted to 2.7 volts by means of potentiometer 312 when a force having a level equal to the predetermined level is exerted on the probe tip.

As shown in the figure, strain gauges 206 and 207 are preferably strain gauge resistors having resistances of 120 ohms when no bending of bending beam 203 is present, resistor 304 is preferably 121 ohms, resistor 305 is preferably 130 ohms, potentiometer 306 is preferably 5K ohms, resistors 307 and 308 are preferably 1.02K ohms, operational amplifier 309 is preferably a National Semiconductor LM725C operational amplifier, potentiometer 310 is preferably 5K ohms, resistor 311 is preferably 101 ohms, potentiometer 312 is preferably 1 Meg. ohms, and LED series 210 preferably comprises eight LEDs.

LED driver circuitry 302 preferably comprises capacitor 315, resistors 316–319, capacitor 320, and dot/bar display driver 321 having an input lead (pin 5 in FIG. 3) and having a plurality of output leads (pins 1, 12–18 in FIG. 3). The input lead is preferably coupled to the output lead of the operational amplifier, and the output leads are preferably coupled to the eight LEDs of LED series 210.

The dot/bar display driver preferably receives the amplifed potential difference signal from the operational amplifier, and lights a selected LED within the series of LEDs in response thereto. The index of the selected LED within the series is preferably proportional to the amplified magnitude of the amplified potential difference signal. The display driver preferably lights none of the LEDs within the series when the amplified magnitude of the amplified potential difference signal is 1.5 volts, but preferably lights the fifth LED within the series when the amplified magnitude is 2.7 volts.

As shown in the figure, capacitor 315 is preferably 0.33 microfarads, resistor 316 is preferably 4.02K ohms, resistor 317 is preferably 12.4K ohms, resistor 318 is preferably 1.02K ohms, resistor 319 is preferably 1.5K ohms, capacitor 320 is preferably 0.33 microfarads, and dot/bar display driver 321 is preferably a National Semiconductor LM3914 dot/bar display driver.

Voltage supply circuitry 303 preferably comprises battery 322, resistor 323, resistor 324, voltage regulator 325 having first and second input leads (pins 1 and 2 respectively in FIG. 3) and an output lead (pin 3 in FIG. 3), capacitor 326, and circuit node 327. The battery is preferably coupled to the first input lead of the voltage regulator, the resistors are preferably coupled to the second input lead of the voltage regulator and the output lead is preferably coupled to the amplifying circuitry and to the LED circuitry.

Voltage regulator 325 produces a voltage signal at circuit node 327 having a magnitude which is a fraction of the magnitude of the voltage of battery 322. The fraction is preferably proportional to the ratio of the resistance of resistors 323 and 324. The magnitude of the voltage signal is preferably sufficient to activate the amplifying circuitry and the LED circuitry. As shown in the figure, battery 322 is preferably seven volts, resistor 323 is preferably 2.67K ohms, resistor 324 is preferably 1.5K ohms, voltage regulator 325 is preferably a National Semiconductor LM317L 3-terminal adjustable regulator, and capacitor 326 is preferably 0.33 microfarads.

As is clear from the above descriptions, an automatically resetting force-sensing dental probe has been provided which solves the various problems posed by such prior art probes and allows efficient, accurate probing of a patient's periodontal pockets.

Additional advantages and modifications will readily occur to those skilled in the art. The invention in its broader aspects is not, therefore, limited to the specific details, representative methods, and illustrative examples shown and described. Accordingly, departures may be made from such details without departing from the spirit or scope of applicant's general inventive concept.

What is claimed is:

1. An apparatus for probing periodontal tissue, comprising:
    a housing for manipulating the apparatus;
    a probe tip for engaging the periodontal tissue at a selected level of force;
    a resilient beam portion connecting the probe tip to said housing, said beam portion extending in a predetermined angular alignment with said probe tip in the absence of force and being bendable from said predetermined angular alignment to another angular alignment in accordance with the force exerted against the probe tip;
    strain gauge means coupled to the resilient beam portion operative to generate an electrical potential representative of the magnitude of the difference between said another angular alignment and the predetermined angular alignment; and
    force indicating means responsive to said generated electrical potential for indicating the amount of force exerted against the probe tip.

2. The apparatus of claim 1, wherein said strain gauge means includes wheatstone bridge circuitry operative to generate said electrical potential.

3. The probe of claim 2 wherein said force-indicating means comprises
    amplifying circuitry coupled to said wheatstone bridge circuitry for receiving and amplifying said potential difference signal to produce an amplified potential difference signal having an amplified magnitude;
    light emitting diode ("LED") circuitry coupled to said amplifying circuitry for receiving said amplified potential difference signal and visibly indicating the amplified magnitude of said amplified potential difference signal; and
    voltage supply circuitry coupled to said amplifying circuitry and to said LED circuitry for producing a voltage signal necessary to activate said amplifying circuitry and said LED circuitry.

4. The probe of claim 3 wherein said wheatstone bridge circuitry comprises a first resistor, a second resistor, and a potentiometer all having first and second leads wherein said first and second leads of said second resistor are respectively coupled to said first and second leads of said potentiometer to form a parallel combination also having first and second leads, and wherein said second lead of said parallel combination is coupled to said second lead of said first resistor to form a first circuit node.

5. The probe of claim 4 wherein said strain gauge resistors comprise first and second strain gauge resistors having first and second leads wherein said first leads of said strain gauge resistors are coupled together to form a second circuit node, and wherein said second leads of said first and second strain gauge resistors are respectively coupled to said first lead of said first resistor and to said first lead of said parallel combination so that said potential difference signal having a magnitude proportional to said bending of said bending beam is produced between said first and second circuit nodes.

6. The probe of claim 5 wherein said magnitude of said potential difference signal is adjusted to zero by means of said potentiometer when no bending of said bending beam is present.

7. The probe of claim 6 wherein said amplifying circuitry comprises operational amplifier circuitry having first and second input leads respectively coupled to said first and second circuit nodes for receiving said potential differential signal, and having an output lead on which is produced said amplified potential difference signal.

8. The probe of claim 7 wherein said LED circuitry comprises
a series of LEDs; and
driver circuitry coupled to said series of LEDs and coupled to said operational amplifier circuitry for receiving said amplified potential difference signal and then selecting and activating a selected LED within said series of LEDs in response thereto.

9. The probe of claim 8 wherein said series of LEDs comprise a plurality of LEDs, wherein each such LED has an index within said series, and wherein the index of said selected LED is proportional to said amplified magnitude of said amplified potential difference signal.

10. The probe of claim 9 wherein said driver circuitry has an input lead coupled to the output lead of said operational amplifier circuitry for receiving said amplified potential difference signal, and a plurality of output leads respectively coupled to said plurality of LEDs.

11. The probe of claim 10 wherein said amplifying circuitry further comprises adjusting means coupled to said operational amplifier circuitry for adjusting said amplified magnitude of said amplified potential difference circuitry.

12. The probe of claim 11 wherein said series of LEDs comprises eight LEDs, and wherein said amplified magnitude of said amplified potential difference signal is adjusted by means of said adjusting means to cause said driver circuitry to select and activate no LEDs within said series when no bending of said bending beam is present, and to select and activate the fifth LED within said series when a force having a predetermined level is exerted on said probe tip causing said bending beam to bend.

13. The probe of claim 12 wherein said adjusting means comprises first and second adjusting potentiometers.

14. The probe of claim 13 wherein said predetermined level of force ranges from 3 to 130 grams.

* * * * *